United States Patent [19]

New, Jr. et al.

[11] Patent Number: 4,653,498
[45] Date of Patent: Mar. 31, 1987

[54] PULSE OXIMETER MONITOR

[75] Inventors: William New, Jr., Woodside; James E. Corenman, Alameda, both of Calif.

[73] Assignee: Nellcor Incorporated, Haywood, Calif.

[21] Appl. No.: 867,005

[22] Filed: May 20, 1986

Related U.S. Application Data

[63] Continuation of Ser. No. 417,312, Sep. 13, 1982, abandoned, which is a continuation-in-part of Ser. No. 414,175, Sep. 2, 1982, abandoned.

[51] Int. Cl.$^4$ ............................................. A61B 5/02
[52] U.S. Cl. .................................... 128/633; 128/666; 128/689
[58] Field of Search ............... 128/633, 634, 666, 689, 128/690

[56] References Cited

U.S. PATENT DOCUMENTS

| 2,706,927 | 4/1955 | Wood | 88/14 |
|---|---|---|---|
| 3,565,058 | 2/1971 | Mansfield | 128/701 |
| 3,638,640 | 2/1972 | Shaw | 128/2 R |
| 3,658,060 | 4/1972 | Eklof | 128/673 |
| 3,895,316 | 7/1975 | Fein | 128/696 X |
| 3,998,550 | 12/1976 | Konishi et al. | 356/39 |
| 4,013,067 | 3/1977 | Kresse et al. | 128/2.05 R |
| 4,038,976 | 8/1977 | Hardy | 128/690 |
| 4,052,977 | 10/1977 | Karn | 128/661 |
| 4,109,643 | 8/1978 | Bond et al. | 128/666 |
| 4,167,331 | 9/1979 | Nielsen | 128/633 |
| 4,266,554 | 5/1981 | Hamaguri | 128/633 |
| 4,424,814 | 1/1984 | Secunda | 128/633 |

FOREIGN PATENT DOCUMENTS

| 1589461 | 5/1970 | France . |
| 8201948 | 6/1982 | PCT Int'l Appl. . |
| 2039364 | 8/1980 | United Kingdom . |

Primary Examiner—Kyle L. Howell
Assistant Examiner—John C. Hanley

[57] ABSTRACT

A display monitor is disclosed for a pulse oximeter of the type wherein light of two different wavelengths is passed through body tissue, such as a finger, an ear or the scalp, so as to be modulated by the pulsatile component of arterial blood therein and thereby indicate oxygen saturation. A tonal signal is emitted having a pitch proportional to the ratio of oxygen saturation and a sequential repetition proportional to pulse. A visual cue consisting of an array of strobed light emitting diodes is flashed having a total light output proportional to the magnitude of the pulse and a sequential flashing rate proportional to pulse rate. A systematic rejection of extraneous or irregular detected data prevents undue sounding of alarms.

3 Claims, 19 Drawing Figures

PULSE OXIMETER MONITOR

This is a continuation of copending application Ser. No. 417,312, filed Sept. 13, 1982, now abandoned, entitled "PULSE OXIMETER MONITOR", which is a continuation-in-part of application Ser. No. 414,175, filed Sept. 2, 1982, now abandoned.

A two fiche microfiche appendix is included herein, consisting of a total of 67 frames.

This invention relates to pulse oximeters and specifically to the photoelectric determination of arterial oxygen saturation in humans with techniques for initializing data, receiving data for processing, setting and triggering alarms all being set forth.

BACKGROUND OF THE INVENTION

Electronic, non-invasive techniques for determination of oxygen content are known. U.S. Pat. No. 2,706,927 to Wood disclosed the computation of oxygen saturation from measurement of light absorption of body tissue at two wavelengths. A "bloodless" measurement was first taken in which as much blood as possible was squeezed from the area where measurement was taken. Thereafter, arterial blood was allowed to flow into the tissue as the condition of normal blood flow was restored. A comparison of the light absorption in the two states provided information on the arterial oxygen saturation of the subject. A series of devices and procedures have been founded using this technology.

In procedures based on this technology, difficulty has been experienced in reliably determining the "bloodless" parameters; due in part to geometrical distortion due to the compression of the tissue; imperfect measurement of this parameter gave imperfect results.

The transmission of light of each wavelength is a function of the thickness, color, and structure of skin, flesh, bone, blood and other material through which the light passes. This attenuation in transmission has been asserted to have a logarithmic characteristic, in accordance with the Lambert-Beers Law.

In a pulse oximeter, the primary material of interest is pulsatile arterial blood. Arterial blood is the only material whose quantity in the tissue varies with time in synchrony with the beating of the heart. Variations in light transmission therefore indicate variations in blood flow permitting direct optical recording of the pulsatile component of arterial blood flow. This ability to separate out the light absorption of arterial blood is especially convenient; since the oxyhemoglobin component of blood is a substance for which the absorption coefficients can be determined, the fraction of any oxyhemoglobin in arterial blood can be determined.

Optical plethysmographs are well known. Such instruments measure pulse rate and provide information on the quantity of blood forced into the tissues on each heart beat. These instruments generally utilize a light frequency near or at the isobestic point where measurement of pulsatile flow is made independent of oxygen saturation. Consequently, they intentionally eliminate information on oxygen saturation.

Following the Wood U.S. Pat. No. 2,706,927 patent, numerous attempts have been directed at eliminating the difficulties connected with arterial saturation measurements using light absorption where the analysis requires the comparing the "bloodless" measurement either artificially induced or naturally occuring during the rest state of the heart cycle with the measurement of fresh arterial blood when fresh arterial blood enters the tissue. For example, the signal received has been divided into its "AC" and "DC" components and passed through a log amplifier before digital analysis of the signal occurs. See Koneshi et al., U.S. Pat. No. 3,998,550. Likewise, a generation at both wavelengths of subtraction outputs has been utilized before digital analysis. Subtraction outputs have been used to eliminate the DC component and to approximate the logarithmic response of the prior art. See Hamaguri, U.S. Pat. No. 4,266,554. Simply stated, because the pulsatile component constitutes a small portion of the total signal of transmitted light, numerous manipulations based on logarithms have been attempted to screen out the unchanging component of the resultant signal before analysis.

U.S. Pat. No. 3,704,706 to Herczfeld et al disclosed use of a single coherent red light source, preferably a laser. Use of a single light source is unable to separate information dealing with the arterial flow component from that dealing with the arterial oxygen component. The output of such a single red light source instrument can only be an indication of the product of blood flow and the saturation level present. Neither blood flow alone or saturation alone can be known.

In all of the above schemes for the measurement of pulse rate, pulse flow and oxygen saturation, the variant or AC component is a small portion of the total absorption occurring. In such circumstances, discrimination of the signal from other possible sources must occur. When it is remembered that measurements of unconscious, partially anesthetized and otherwise non-responsive patients must occur, and such patients have random and irregular movements (and heart beats), the establishment of thresholds for the reception and analysis of data is critical.

SUMMARY OF INVENTION

A display monitor is disclosed for a pulse oximeter of the type wherein light of two different wavelengths is passed through body tissue, such as a finger, an ear or the scalp, so as to be modulated by the pulsatile component of arterial blood therein and thereby indicate oxygen saturation. The disclosed instrument first receives and compares signal to parameters to check for a pulse like signal. Assuming that a pulse like signal is detected a tonal signal is emitted having a pitch proportional the ratio of oxygen saturation and a sequential repetition proportional to pulse. A visual cue consiting of an array of strobed light emitting diodes is flashed having the number of lights strobed increase with increasing magnitude of the pulses and having a sequential flashing rate proportional to pulse rate. A systematic rejection of extraneous or irregular detected data prevents undue sounding of alarms.

OTHER OBJECTS, FEATURES, AND ADVANTAGES OF INVENTION

An object of this invention is to disclose an instrument which can simultaneously trace and indicate the pulse as well as the degree of oxygen saturation of the individual. According to this aspect of the invention, at least one of the wavelengths of light, preferably infrared, is monitored for slope change. A signal is emitted proportional to and typically synchronous with the slope change rate to indicate heart rate. A second signal is emitted containing pulse rate and oxygen saturation information.

An advantage of this aspect of the invention is that each pulsatile component is individually analyzed. The heart beat and arterial oxygen level of the patient is continually monitored.

Yet another object of this invention is to disclose a series of audible signals which convey pulse rate and oxygen saturation. Pulse rate is indicated by emitting sequential tones at time intervals corresponding to the rate of negative slope reversals (indicating pulse wave maximum). Oxygen saturation is indicated by having pitch decrease proportional to decreasing oxygen saturation.

An advantage of this aspect of the invention is that the human ear is particularly sensitive to both changes in frequency of sequential sound signals and tonal variations in sequential sound signals. A simple beating signal can make all in the immediate vicinity well aware of both the pulse rate and oxygen saturation of the patient.

Yet another aspect of this invention is to emit a visual signal conveying similar information. According to this aspect of the invention, a column of light emitting diodes flashes in height proportional to pulse magnitude and flashes in frequency proportional to pulse rate. As the eye is particularly sensitive to changes in both flashing rate and angular dimension or height of the flashing LED array, an indication of pulse quality is given.

Yet another object of this invention is to disclose a plurality of alarms, which alarms can all be individually set in accordance with the current condition of the patient. According to this aspect of the invention, high pulse rate, low pulse rate and oxygen saturation levels can all be utilized as an alarm limit.

An advantage of this aspect of the invention is that the parameter of the patient's warning limits can be tailored by the anesthesiologist or other attending physicians. Individual adjustment can be made to the particular physiology present.

Yet another object of this invention is to disclose a regimen in combination with the instrument for rejecting extraneous data. Remembering that patients are often in an unconscious or semi-conscious state when this instrument is used, it can be realized that the instrument does not operate in a perfect environment. Shaking or moving the sensor head or even local variations in the patients pulsatile profile could unnecessarily trigger alarms. According to this aspect, incoming processed data is compared to confidence factors. If the data falls within expected levels, confidence factors remain unchanged or are upgraded to the highest level. Where data falls without the anticipated confidence levels, the data itself may be rejected. The confidence levels are eroded or opened in the range of data that can be processed. This process occurs until data consistent with the confidence limits is received. When data consistent with the confidence factor is received, it is compared to the alarm limit.

An advantage of this aspect of the invention is that small local variations in the received signal do not trigger the alarms.

Yet another aspect of this invention is to disclose a totality of data utilized for tracking the pulse. According to this aspect of the invention, the points of maximum light transmission (commencement of inflowing pulse) and maximum light absorption (end of arterial pulse) are tracked for at least one wavelength. A maximum negative slope intermediate the maxima and minima is plotted for avoidance of the dicrotic notch. Finally, the percent of oxygen saturation is determined by comparison of light transmission at both frequencies.

All of these data are analyzed against the confidence limits for reception. Where three out of the six data values are outside the limits, the entirety of the data is rejected. Where four or more of the data values are within, the data is received and the confidence limits under the acceptable catagories upgraded or maintained at the narrowest limit. Confidence limits of unacceptable data are eroded or opened.

An advantage of this aspect of the invention is that interruption of data often occurs at more than one parameter. With such interruption, the entire data block may be averaged to prevent the premature sounding of alarms.

A further object of this invention is to disclose a simplified control for adjusting alarm limits. According to this aspect, adjustment occurs to a shaft encoder directly coupled to an alarm limit adjustment knob. The alarm limit to be set is selected by pressing at least one selector button. Thereafter, turning of the alarm limit adjuster knob updates the limit by sign—depending upon direction of turn—and in limit—depending upon amount of turns. The current alarm limit being changed is shown in the visual display. If the alarm limit does not change for a preset period, that is, the knob is no longer being turned, the knob to the alarm limit is disconnected and the knob is again connected to its original connection and the display returns to its original status.

An advantage of this aspect of the invention is that alarm limit control is easily and simply adjusted. The complex environment of the operating room and intensive care unit is provided with a useful instrument having simplified adjustment. In particular, the alarms can be controlled by one hand, important in some aspects of patient care. It is not necessary to manually reset the instrument to its original status of displaying saturation or pulse rate.

Other objects, features and advantages of this invention will become more apparent after referring to the following specifications and attached drawings in which:

DESCRIPTION OF THE PREFERRED EMBODIMENT

Figure 1:
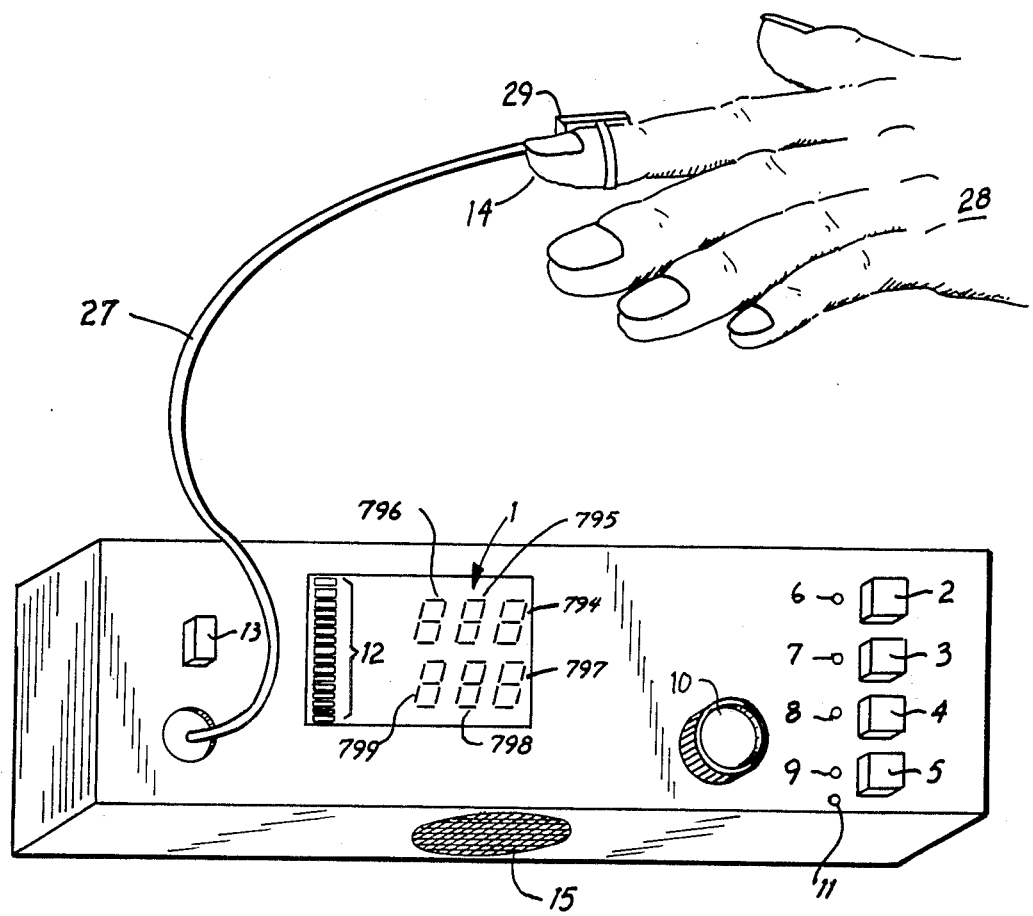
FIG. 1 is a perspective view of the instrument of this invention illustrating the instrument housing and attachment of a sensor to the digit of a patient.

Referring to FIG. 1, the instrument housing 26 of this invention is illustrated. Outwardly, the housing includes a digit display 1, circuitry select button array 2 through 5, alarm status lights 6 through 9, an optically coupled adjustment knob 10, sync status light 11, LED digital viewmeter 12, and power switch 13. A speaker 15 is placed under and in the instrument housing.

From a connector (not shown) in housing 26 there extend leader wires 27. Wires 27 extend to a detector probe 29. Detector 29 is placed upon the finger 14 of a patient 28. Utilizing the placement of the detector 29 at the finger 14, all of the readings in this invention are made possible.

Oximeter Operation

Figure 2:
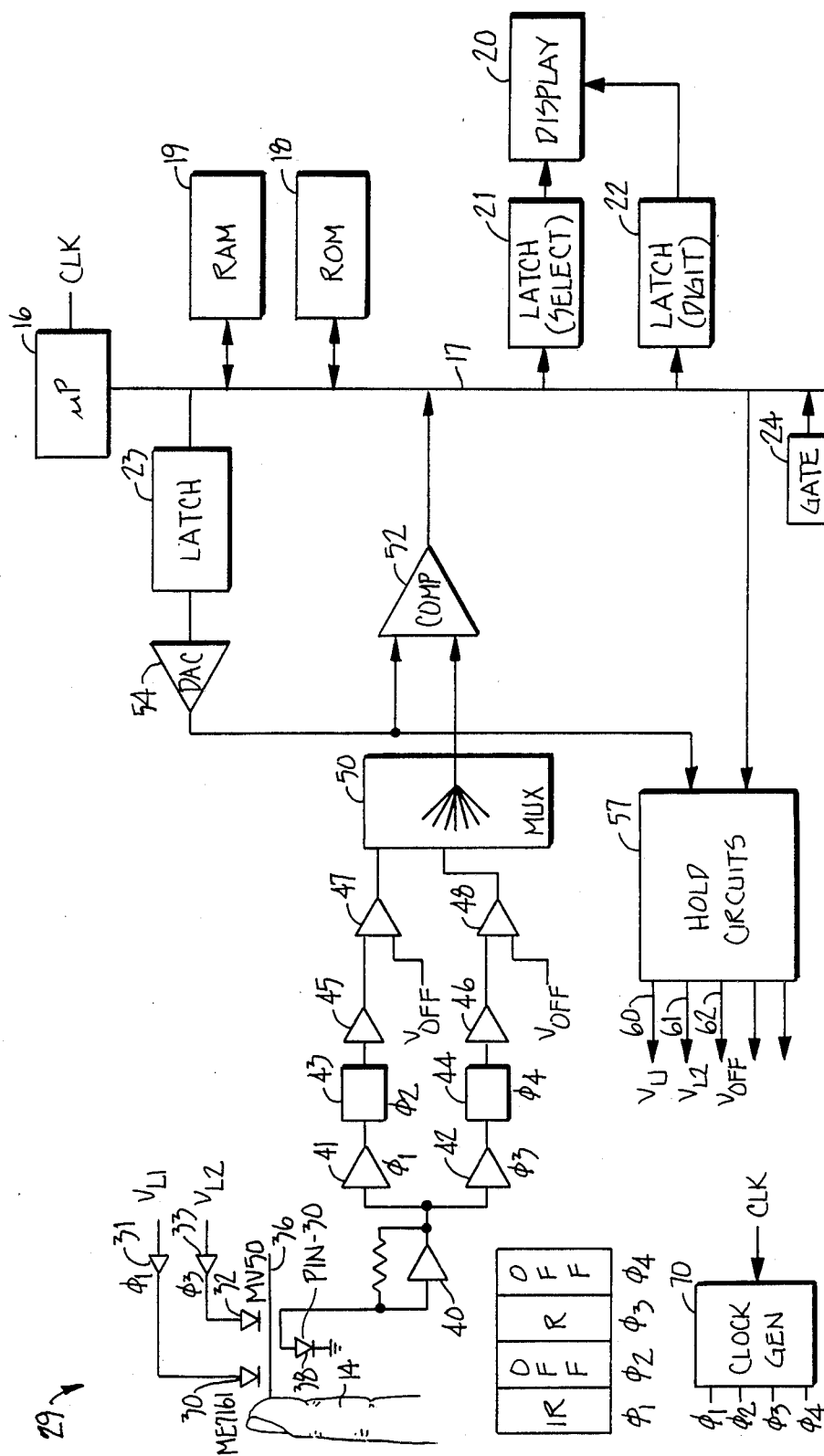
FIG. 2 is an overall circuit schematic of this invention.

A broader view of the operation of this invention can be made by considering carefully the circuit schematic of FIG. 2.

Referring to FIG. 2, conventional microprocessor 16 has a bus 17 extending therefrom. Bus 17 has connected thereto conventional ROM 18 and RAM 19. An LED display 20 is schematically illustrated having a select latch 21 and a digit designation latch 22. The circuit select button array 2-5 and optically coupled control knob 10 previously illustrated are gated through controls generally denominated 24.

Having set forth the more or less conventional portions of the microprocessor, attention will now be directed to the analog portions of the circuitry.

Finger 14 of patient 28 is illustrated with detector 29 having schematic detection circuitry. First light emitting diode 32 in the red range and a second light emitting diode 30 in the infrared range are sequentially pulsed to emit light in their respective frequencies by amplifiers 31,33. Typically, LED 32 is in the 660 nanometer range with LED 30 being in the 940 nanometer range.

It is necessary that all the light from the active light emitting diode go through the flesh in finger 14. Therefore, a light impervious barrier 36 is placed between photosensor 38 and finger 14. Barrier 36, terminating in contact with the flesh of finger 14, makes the path between the respective light emitting diodes 30, 32 and the light receiving diode 38 occur only through the flesh of finger 14.

In the instrument herein we utilize two discrete wavelengths. These wavelengths are 660 nanometers (red) and 940 nanometers (infrared). A small amount of discussion related to these parameters is in order.

First, the wavelengths are chosen so that they are far enough apart so that the transmission of light appreciably varies with changes in oxygen saturation.

Secondly, the wavelength are chosen so that the same tissue is sampled. For example, a wavelength in the ultraviolet would not sample the same tissue due to scattering.

While wavelengths extremely close could be used, we have chosen not to do so. We find that drifting of light source wavelengths can occur with accompanying problems.

Signal received from the respective light emitting diodes first passes through a pre-amplifier 40. This signal is thereafter amplified in parallel at amplifiers 41, 42. As amplified, the signal is passed in parallel from each amplifier through respective phase detectors 43, 44. Passage through respective low pass filters 45, 46 thereafter occurs. Amplification at offset amplifiers 47, 48 then takes place. The pulsatile component is passed to multiplexer 50.

Multiplexer 50 has output to a comparator 52. Comparator 52 is ramped in half steps by a 12 bit digital to analog converter (hereinafter DAC) 54. DAC 54 places a comparison signal divided in one part from 4096 parts with the comparator outputting to bus 17.

The reader will recognize that not all human fingers and appendages are the same. Specifically, the difference between the races, skin pigment, weight, age, maturity and other factors all can lead to different signals being sensed at photosensor 38, even though the wavelength and intensity of the light signal output at each of the diodes 30, 32 is the same.

Accordingly, microprocessor 16 is programmed to receive a signal from photosensor 38 within an optimum range. Utilizing a second operating phase of DAC 54, and communicating signal to a sample hold 57, the individual LED's 30, 32 are given voltage outputs 60, 61. These voltage outputs 60, 61 are adjusted so that in each case photosensor 38 looks at a signal well withing the range of the DAC.

Clock 70 controls the sequential output of light from the light emitting diodes 30, 32 to a duty cycle of at least 1 in 4. This is schematically illustrated by signals $\phi 1$ through $\phi 4$. Reception of signal at detector 43 occurs during time periods $\phi 1$ and $\phi 2$ and reception of signal occurs at detector 44 during time periods $\phi 3$ and $\phi 4$.

It can be immediately realized that during respective time periods $\phi 1$, $\phi 3$ active signal from the light emitting diodes 30, 32 is being received. During the time periods $\phi 2$ and $\phi 4$ no signal and only noise is being received. As will hereinafter become apparent, by amplifying the negative signal before passage through the low pass filter, noise can be subtracted out utilizing the illustrated 1 in 4 duty cycle.

Having given the reader an overview of the circuitry utilized with this invention, the invention will now be discussed in detail.

Figure 3:
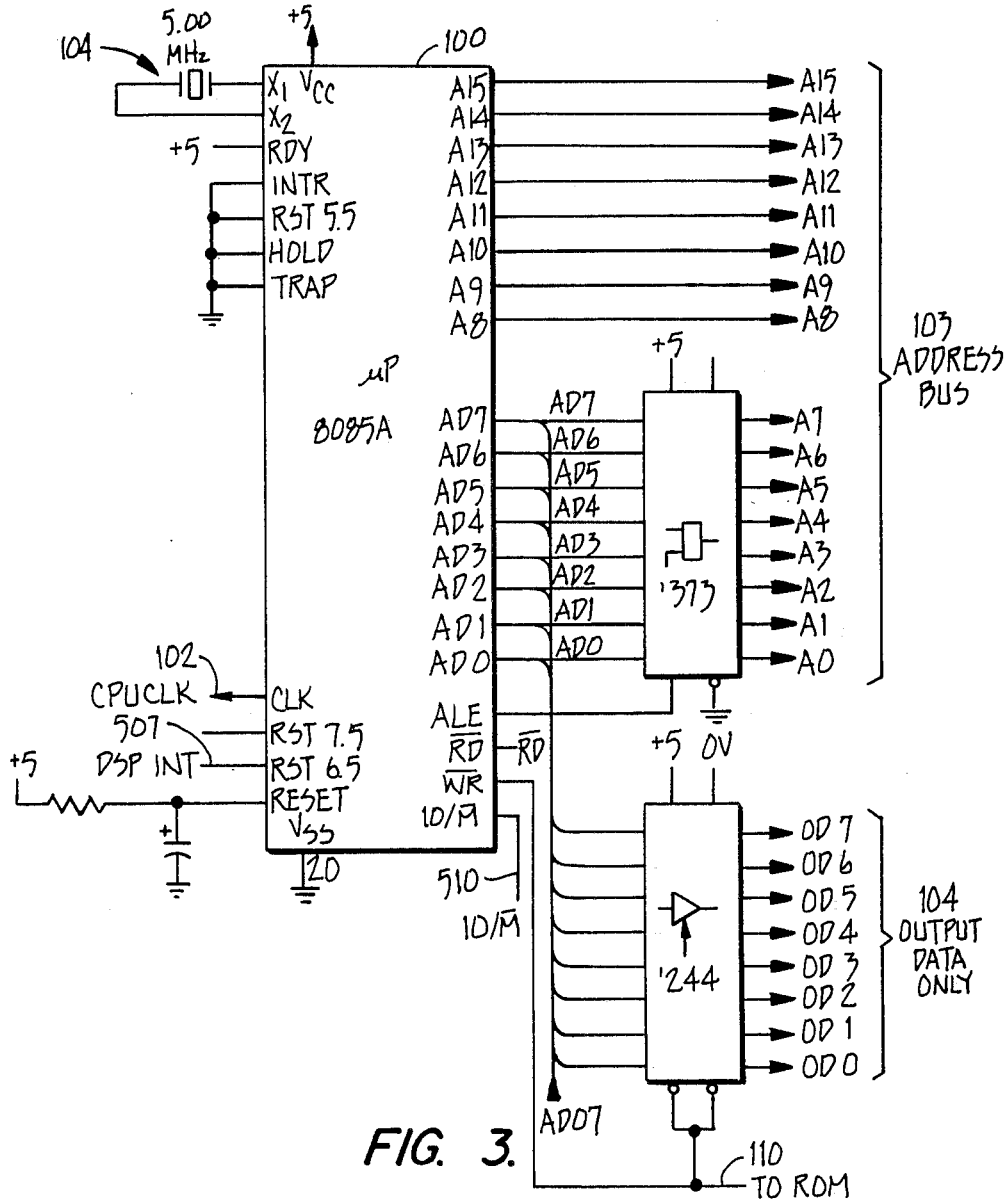
FIG. 3 is a circuit schematic in the vicinity of the microprocessor.

Referring to FIG. 3, the microprocessor 100 is illustrated having an attached crystal 104. This crystal, in combination with clock circuitry incorporated within the microprocessor 100, generates the clock signals required by the microprocessor chip itself as well as providing clock pulses to the rest of the oximeter circuitry through output 102.

Microprocessor 100 is an 8085A CPU integrated circuit chip available from Intel Corporation of Santa Clara, Calif. The family identification suffixes of the remaining IC components are listed on the drawing and the components are readily available from various manufacturers.

An address bus 103 includes address lines A0 through A15. To accommodate the eight bit processor, lines A0 through A7 on the address bus are latched from microprocessor pins AD0 through AD7 so that during the address time state these lines may be read. During an alternate time state, lines AD0 through AD7 become output data lines 104, OD0 through OD7, which lines as here configured are only capable of outputting data.

Figure 4:
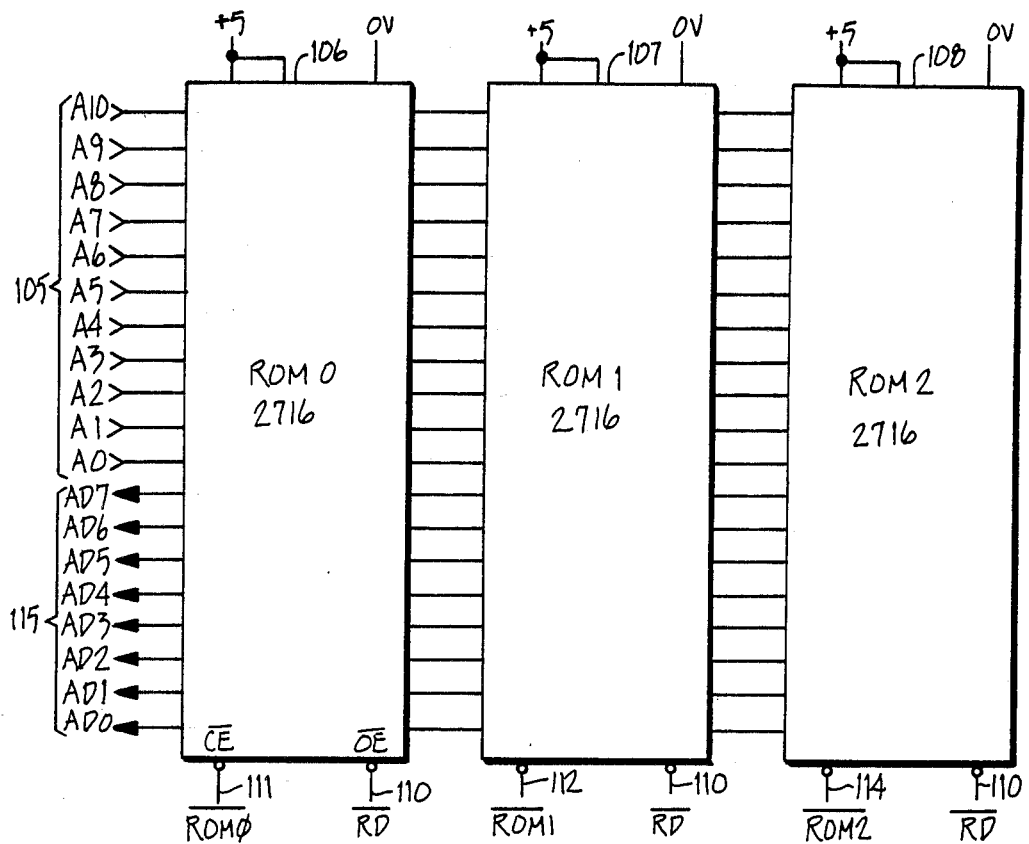
FIG. 4. is a circuit schematic in the vicinity of the read only memory or ROM of this invention.

Referring to FIG. 4, the ROM configuration is seen to be standard. The ROM is addressed with a conventional address bus including lines A0 to A10 addressing in parallel ROMs 106, 107 and 108. These respective ROMs are enabled by three decoded address bits from lines A11–A13 (see FIG. 6). As will hereinafter be set forth with respect to FIG. 6, enabling outputs for reading of the ROMs include read enable 110 (see FIGS. 3, 4) and specific ROM addresses including ROM 0 address 111, ROM 1 address 112, and ROM 2 address 114. The particular ROMs here utilized are of the optically erasable programmable read only memory variety and include an output data bus 115.

Figure 5:
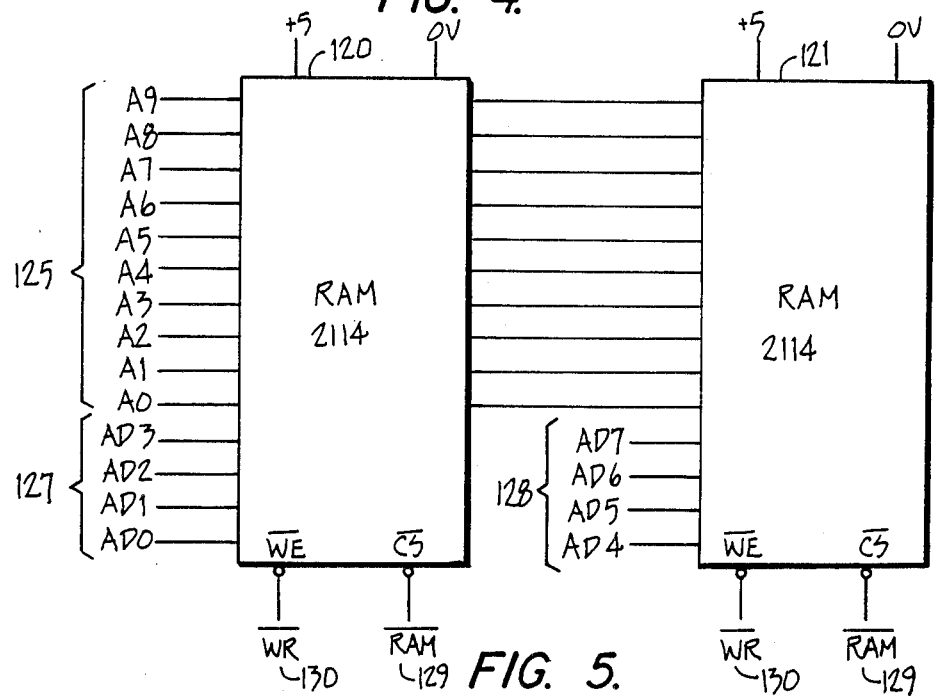
FIG. 5 is a circuit schematic in the vicinity of the random access memory or RAM of this invention.

Referring to FIG. 5, two conventional RAMs 120, 121 are shown addressed in parallel at address bits A0 through A9 at bussing 125. These RAMs write and read over eight bits with four bus lines AD0 to AD3 at bus 127 addressing RAM 120 and AD4–AD7 addressing RAM 121 at bussing 128. RAMs 120, 121 are read when enabled through enable ports 129 in the absence of a write signal on port 130. These RAMs are written when enabled by port 129 in the presence of a write signal through write ports 130. As each of the RAMs connect to four separate data bits, individual enabling of each of the RAMs is not required.

Figure 6:
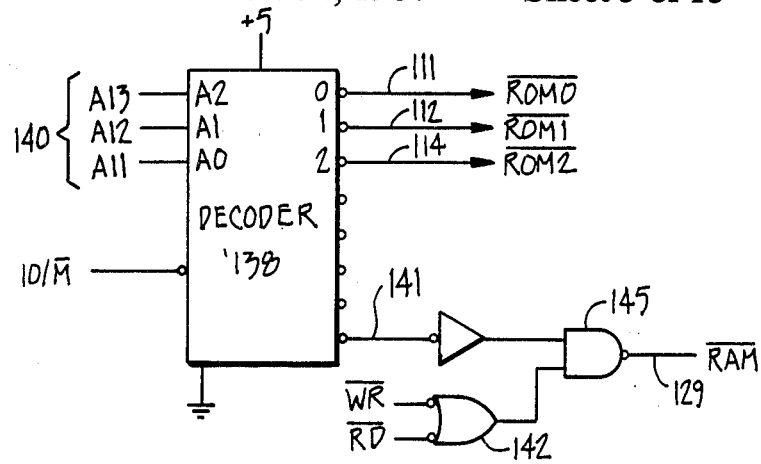
FIG. 6 is a circuit schematic of the memory select.
Figure 7:
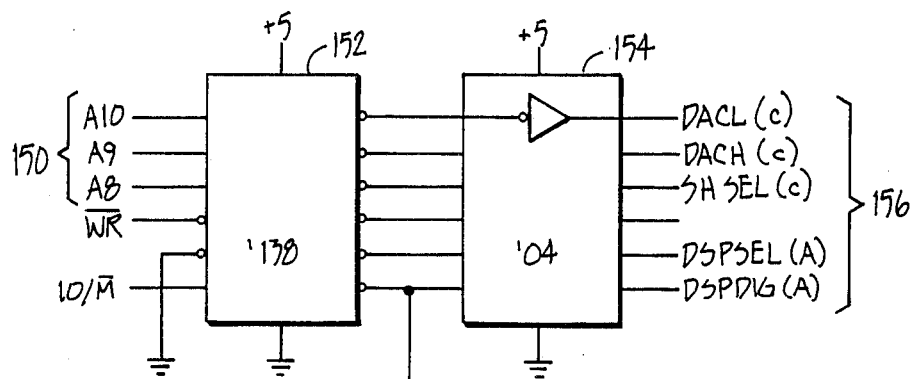
FIG. 7 is a circuit schematic of the input/output select.

Referring to FIG. 6, the memory select circuit of this invention is illustrated. The memory select has a three bit input 140 at lines A11–A13. Output occurs when memory is selected at ROM 0 enable 111, ROM 1 enable 112, ROM 2 enable 114. A RAM enable 141 passes through an inverter and NAND gate to enable reading of RAMs 120, 121 for either reading or writing.

Figure 8:
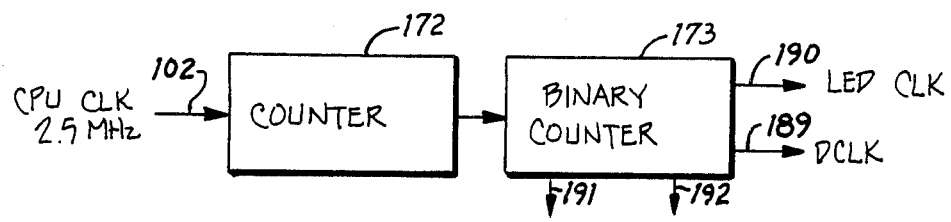
FIG. 8 is a circuit schematic of the counter of this invention.

Referring to FIG. 8, a counter used as a divider is illustrated. Referring briefly back to FIG. 3, it will be seen that the microprocessor 100 is provided with a clock running at 2.5 MHz generally denominated 102. The CPU clock outputs at 102 to a counter 172 (see FIG. 8.) Counter 172 divides signal 102 by the number 171 and outputs to binary counter 173 in order to generate an LED clock frequency of 1.827 kHz, which is unrelated to room light frequencies. Counter 173 outputs signals LED A 191, LED B 192, LED CLK 190 and DCLK 189. This circuit in cooperation with the circuit of FIG. 13, effects light and detector switching to enable signal phasing.

Having set forth in generality the microprocessor, it will be realized that much of that disclosed is already known in the art. Specifically, complete descriptions of the wiring of this microprocessor can be found in the MCS-8085 Family Users Manual, published October 1979 by Intel Corporation. Those having skill in the art are referred to this publication should question arise about the circuitry thus far described.

Figure 13:
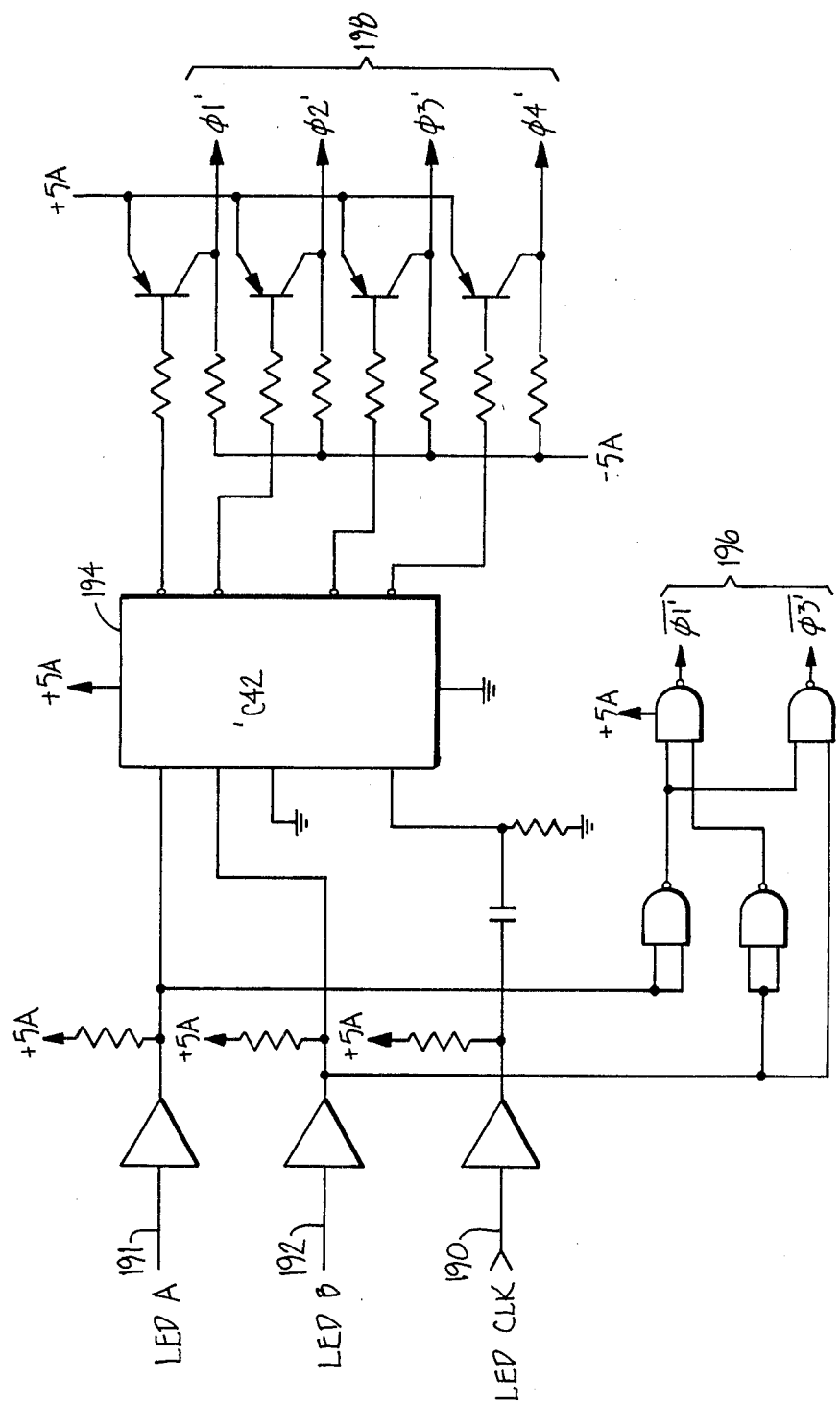
FIG. 13 is a detail of a clock circuit having an output for powering the light emitting diodes.

Referring briefly back to FIG. 8, LED clock outputs 190, 191, 192 are inputed to the clock divider 194 of FIG. 13. Divider 194 outputs four sequential duty cycle states denominated $\phi1'$ through $\phi4'$. Complements of signals $\phi1'$ and $\phi3'$ are outputed directly at clock driver outputs 196. It will be noted that all four signals $\phi1'$–$\phi4'$ are outputed at 198 for timing purposes hereinafter discussed.

Having set forth the timer, the remainder of this disclosure will be broken down into five discrete parts. First, timing for the light emission of the LED's will be discussed. Emphasis will be placed on the fact that the diodes are switched locally.

Second, light reception will be set forth. With respect to the reception, emphasis will be made to the fact that the signal is digitally extracted without any analog treatment whatsoever. The pure digital signal is thereafter processed and utilized to create the light curves herein. Effort is made to eliminate all variables present, including those in the flesh analyzed as well as ambient light noise.

Thirdly, and in view of variant light transmission qualities of human flesh, the light level adjustment circuit of this invention will be traced. It will be pointed out that the adjustment of the emitted light occurs so that the sensor receives an amount appropriate for the amplification circuitry.

Fourth, setting of the alarm limits will be analyzed. Illustration will be made.

Fifth, and finally, the program alarm will be discussed. Specifically, the utilization of "confidence limits" and a totality of data received in the monitoring program will be disclosed as screening extraneous data yet permitting a timely alarm to ward off catastrophe.

Figure 14:
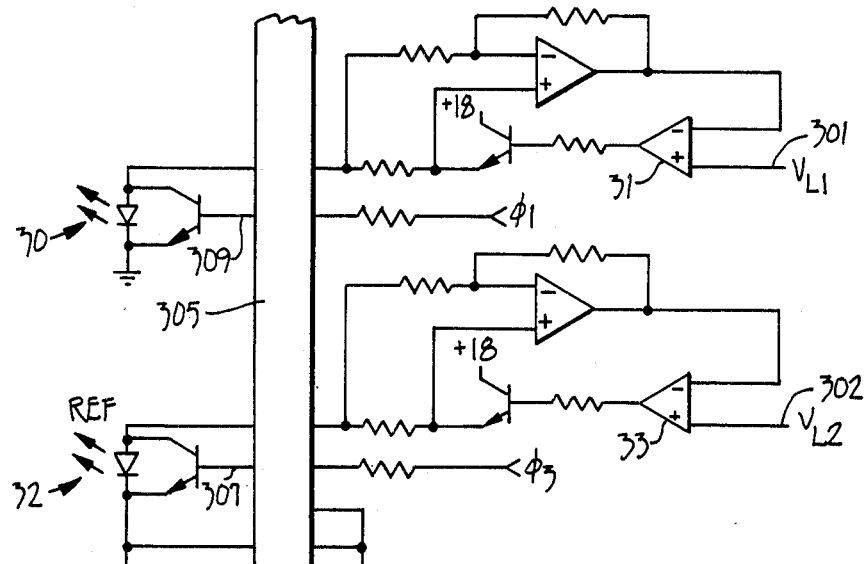
FIG. 14 is a detail of circuitry for powering the light emitting diodes, the diodes being switched at a point proximate to the detector.

Referring to FIG. 14, and assuming that sufficient voltage is present across leads 301, 302, current of an appropriate level will be emitted to each of the light emitting diodes 30, 32. The diodes here are illustrated schematically across a connector 305 and are shown being switched by respective transistors 307, 309. Specifically, when a negation pulse is received at each of the transistors, the transistors open, voltage appears across the respective diodes 30, 32, and light is emitted.

Assuming light is transmitted, it is passed to the flesh of the digit 14 and is thereafter received at the receiving photosensor 38.

Figure 12:
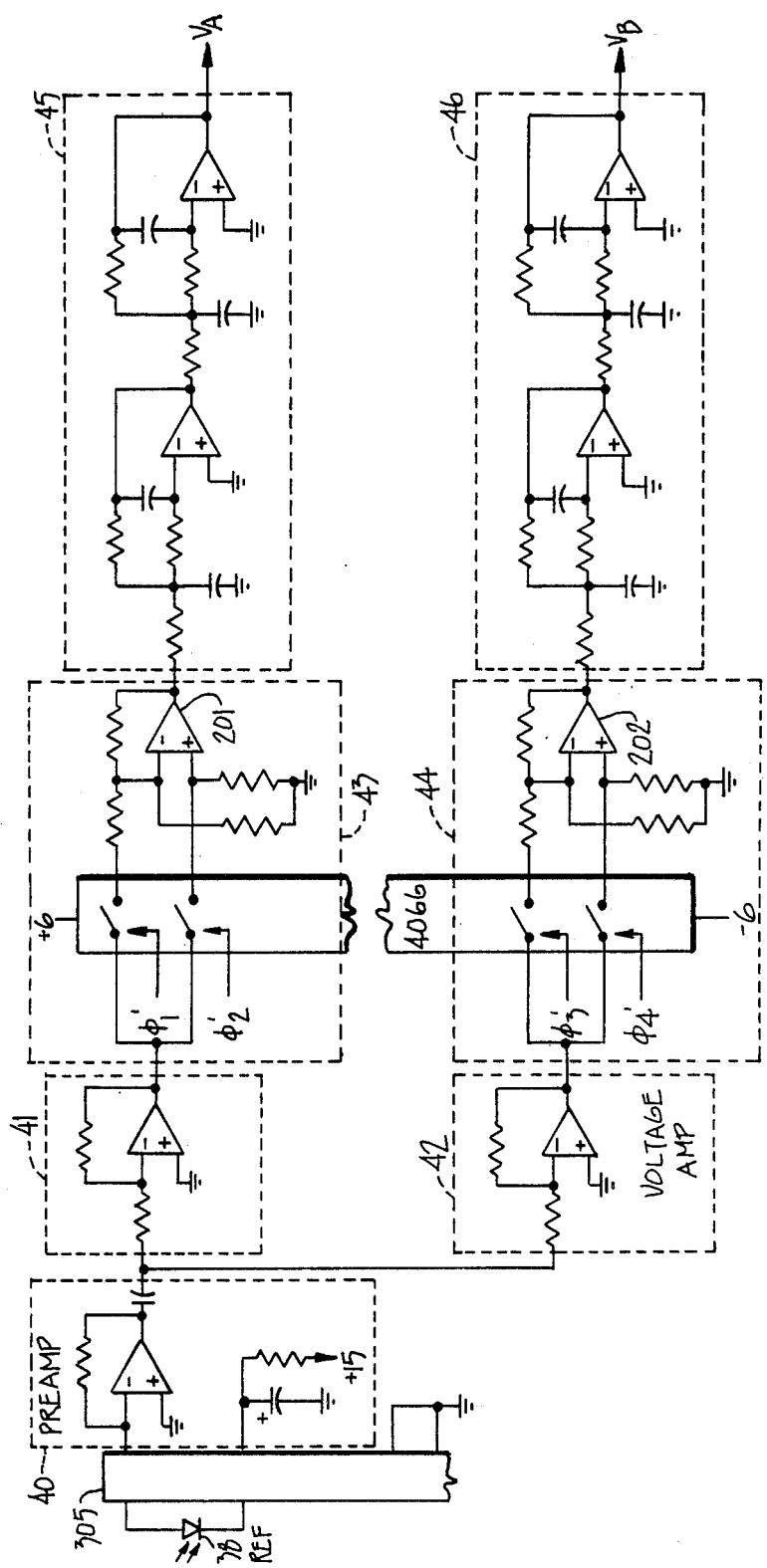
FIG. 12 is a circuit schematic of the detector of this invention.

Referring to FIG. 12, photosensor 38 is illustrated. It is coupled across a connector 305. Connector 305 in turn passes its signal through amplifier 40. The signal is then split and passed to voltage amplifiers 41, 42, the amplification here occurring in parallel, allowing differences in gain between red and infrared signal processing. Respective phase detectors 43, 44 are clocked at inputs $\phi1'$–$\phi4'$ from the clock circuit of FIG. 13. Remembering that a 1 in 4 duty cycle is here utilized with each of the signals $\phi1'$, $\phi2'$, $\phi3'$, $\phi4'$ being clock periods, it is seen that the signal is gated. Specifically, and during the $\phi1'$ time period, negative amplification of the total light signal, including pulsatile component and noise, occurs at amplifier 201 with passage of the resultant signal through the low pass filter 45.

Referring to FIG. 14, in the next sequential time period, and due to the signal $\phi1'$ no longer appearing to close transistor 309, transistor 309 will be shunted to ground. At the same time, during time period 02' gate 43 will open to amplify the positive component received. This component received, however, will have no light emission whatsoever; it instead will represent pure electronic or optical noise. The timing of this circuit will therefore yield on equal bases first light containing the pulsatile component and noise and thereafter just noise. Amplifier 201 amplifies one signal positively and the other signal negatively in equal amounts. It will be seen that integrated over the full four periods of the clock, through amplifier 201 the instrument sees equal components of noise which cancel and unequal components of signal which do not cancel. By the expedient of taking the respective intermittent pulses and passing them through the low pass filter 45, there results a signal out containing valid signal only; noise cancels.

The remaining channel is analogous. Specifically, during time period $\phi 3'$, noise and light signal are amplified negatively and passed through low pass filter 46. During time period $\phi 4'$, noise only is positively amplified and cancelled in passage through the low pass filter 46.

The emitted signal $V_A$ and $V_B$ can be described as having two components. The first component is constant. It is that element of light which remains essentially invariant. This signal includes an absorption component because of skin pigment, bone, flesh and venous blood. The second component represents the pulsatile inflow of arterial blood.

The ratio of that second component to the first component is what is sought by the instrument. What is sought is the ratio of the arterial and pulsatile component of the blood to that of the total absorbing tissue. The color of the arterial component of the blood produces the differential light absorption that is dependant upon the oxygen saturation of the hemoglobin. The instrument must isolate this component.

Figure 11:
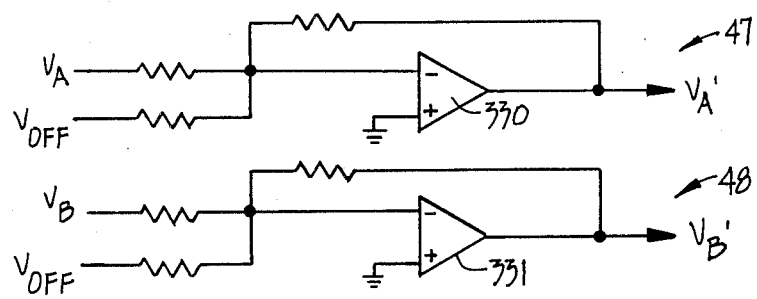
FIG. 11 is a circuit schematic of the offset amplifier circuit of this invention.

Referring to FIG. 11, amplification of the signal to an idealized state is illustrated. Specifically, in taking respective signals VA', VB', an offset voltage VOFF introduced. This signal is a constant voltage which subtracts out part of the constant portion of the received light signal which relates to passage through the nonvariant portions of the flesh. Since it is known that the pulsatile component is always very small with respect to the total signal, an improvement on the accuracy of digital conversion can be obtained by this subtraction. It is necessary, however, for the microprocessor program to mathematically reinsert this subtracted voltage prior to processing the signal. This subtraction and amplification occurs at the respective amplifiers 330, 331 with passage of the signals VA' and VB' from the network.

With digital to analog conversion of these signals, a combination of the pulsatile component and the remainder of the constant component is then required. This can best be seen through the circuitry of FIG. 9.

Figure 9:
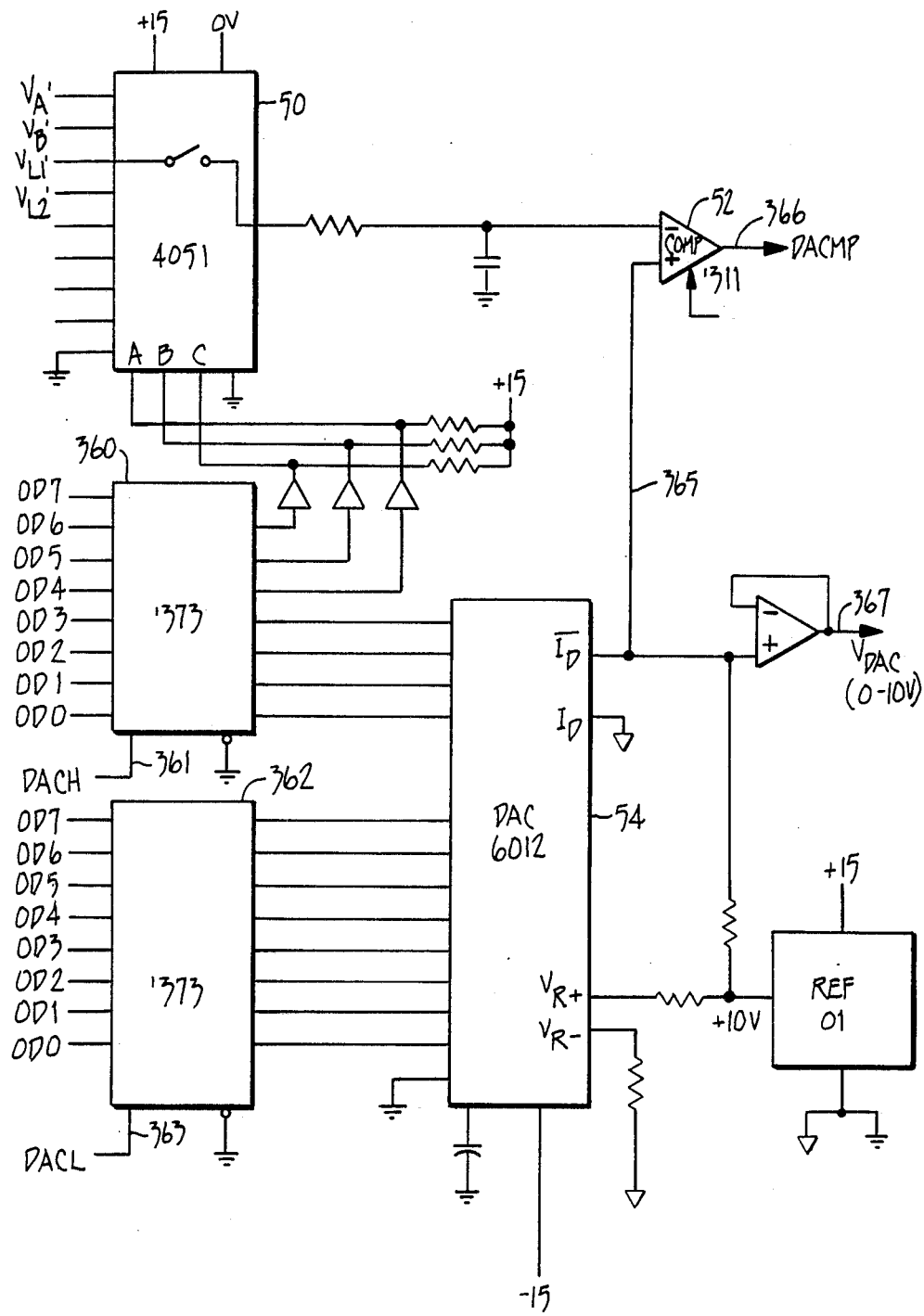
FIG. 9 is a circuit schematic of the comparator circuit wherein 12 bit digital to analog conversion occurs.

Referring to FIG. 9, a multiplexor 50 is illustrated. During the analytical operation here shown, this multiplexor samples signals VA' and VB'. Signal is passed to the negative side of comparator 52. Signal for driving the multiplexor passes through lines OD4–OD6 in the DAC high latch 360. The DAC low latch 362 is thereafter actuated in sequence responsive to enabling signals on enabling line 363. Output occurs to a digital to analog converter 54 on a twelve bit basis. Division to one part in 4096 occurs.

Typically, the signal is compared in halves. Output of DAC 54 occurs over lead 365 to comparator 52. The comparator output 366 is passed to the microprocessor. Depending upon whether a high or low signal is received, stepping of the twelve bit DAC 54 occurs in halves, enabling the twelve bit division to occur rapidly. Consequently, the output level of the voltage of the receiving photosensor is rapidly determined with the result that the pulsatile component can be rapidly followed. This process is repeated for both signals VA' and VB' at a rate that allows the microprocessor to faithfully track both signals.

Having set forth the light reception circuitry of this invention, attention will now be directed to the level of light adjustment.

Figure 10:
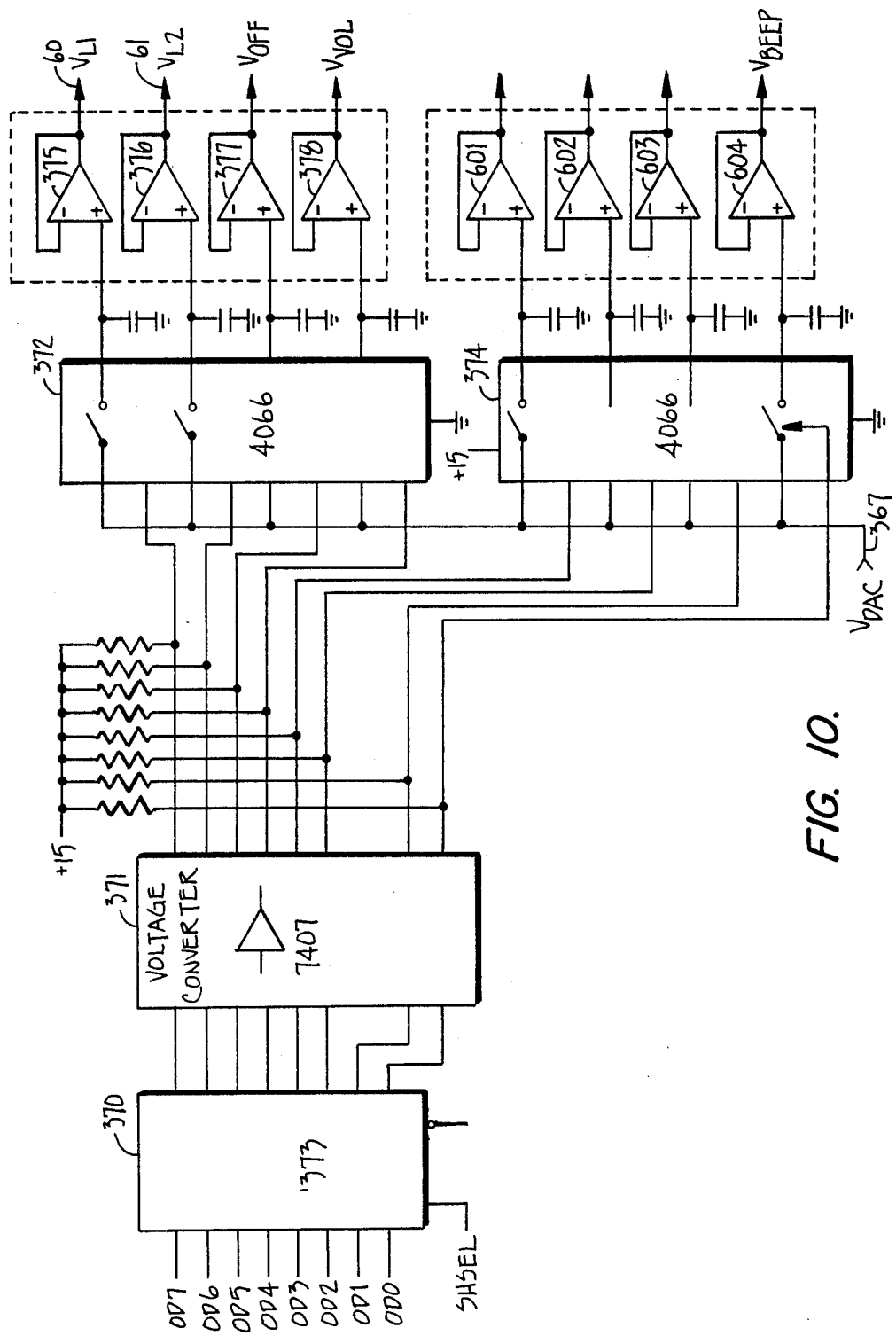
FIG. 10 is a circuit schematic of the sample-hold circuitry of this invention.

It will be remembered that each of the patients, due to flesh, skin pigment, skin thickness, bone, venous blood present and other invariants, will present his own factor of constant light absorption at both wavelengths. This being the case, it is necessary to adjust the level of current applied. This is done through the DAC circuit of FIG. 9 and the sample hold circuit of FIG. 10.

The sampling of the light signals by the microprocessor was described above. In the case where the signals are not within the useful range of the conversion circuitry, the light level must be adjusted up or down as required to restore the signal level to the voltage range acceptable to the analog to digital conversion. Referring to FIG. 9, the program will output a code corresponding to the desired voltage level through its data bus into latches 362 and 360, setting the DAC 54 output to a voltage corresponding to desired LED current. Note that this is only done during a time period when the DAC is not used for input conversion. The program will then output using the same bus a bit corresponding to the selected LED into latch 370 of FIG. 10. This bit, or selection signal, is converted to a compatible voltage by voltage converter 371 and applied to one of eight analog switches 372 and 374. These have the effect of applying the voltage from the DAC, corresponding to the desired LED current level, to a storage capacitor which will latch this voltage after the input has been removed. This voltage is buffered by amplifiers 375 and 376 and applied to the LED circuitry. Thus, dependant upon the intensity of the signal received by the photosensor, the respective light emitting diodes can be driven with greater or lesser voltage to produce the optimum voltage output.

It is noted that only two of the available eight channels of this sample hold circuitry are required to adjust the LED intensities. The remaining channels provide a general purpose analog output from the microprocessor for a variety of unrelated functions. The output of amplifier 377 provides the fixed offset for the offset amplifiers described above; VVOL, the output of amplifier 378, provides a volume control for the alarm; outputs of amplifiers 601, 602, and 603 provide external outputs for an optional chart recorder; and the output of amplifier 604 provides a control for the pitch of the alarm.

Monitor Operation

The manner in which the signal information derived by the oximeter apparatus is presented to the attendant physician through the oximeter monitor of this invention will now be discussed.

Referring to FIG. 1, when the instrument power is turned on via power switch 13, digit display 1 and LED digital viewmeter 12 both flash momentarily until microprocessor 16 begins its operation. Speaker 15 also emits a beep. As soon as the microprocessor 16 takes control of the instrument, which is on the order of a millisecond, the digit display 1 is cleared, with zeros flashing on digits 794–796. On power up, the oximeter default is for the audio alarm to be inhibited so that LED alarm inhibit light 9 begins flashing. Synchronization of the pulse rate of patient 28 through detector probe 29 is not yet established. Therefore, the sync status light 11 flashes, indicating no sync. Microprocessor 16 begins to sample the signals from photosensor 38 until it determines that valid pulses are being received, at which point digits 794–796 of digit display 1 indicate in decimal numbers the percentage of oxygen saturation in the patient's 28 blood. Digits 797–799 numerically indicate the pulse rate. The LED digital viewmeter 12 begins to flash synchronously with the pulse rate with the vertical height of each flash being proportional to the strength of the received pulse. After about 4 or 5 valid pulses have been received no-sync LED light 11 is disabled and switches off. The alarm, which operates when triggered through speaker 15, may be manually enabled by the user at this point, through alarm button 5. When button 5 is pressed, alarm inhibit light 9 ceases to flash. The alarm will sound when the alarm limits are exceeded as discussed in detail below.

When pulse synchronization is achieved, speaker 15 begins emitting beep tones at a frequency synchronous with that of the perceived pulse rate and at a pitch proportional to oxygen saturation. Defaults provide an initial volume and pitch to these signals.

The information is updated from the microprocessor 16 on a continual and regular basis, modified only by a digital filter which serves the purpose of averaging recent pulse history with present information. This simply serves to smooth out transient small deviations in pulse rate and oxygen saturation due to physiologic and artifactual noise variations.

The microprocessor 16 continues to sample data and compare it to the current alarm limits in the instrument. Upon power up, in the presently preferred embodiment the alarm limits are defaulted to an 85% lower oxygen saturation limit, a lower pulse rate limit of 55 and an upper pulse rate limit of 140.

The alarm limit defaults and the audio signal from speaker 15 may be changed in the following manner. The volume of the beep tone from speaker 15 can be set by the user by turning optically coupled control knob 10 (FIG. 1). Turning control knob 10 clockwise will enable volume to be maximized; turning knob 10 counter-clockwise can enable the audio output of speaker 15 to be totally inhibited.

To alter an alarm limit parameter, one of buttons 2–4 is pressed. For example, when saturation limit button 2 is pushed, the current saturation level alarm limit is displayed on digit 794–796. Initially, that will be the defaulted limit of 85. Optical knob 10 is then enabled for adjustment of oxygen saturation limit. By turning knob 10 in either direction, that limit may be changed anywhere from 0 to 100%, depending on what the clinician decides is an appropriate saturation alarm for the patient's situation. After about two seconds of inactivity on knob 10, knob 10 will automatically be disabled for saturation limit adjustment and will return to the volume adjustment mode. Concurrently, the display 1 is switched back to show the current oxygen saturation level and the current pulse rate. High pulse rate limit button 3 and low pulse rate limit button 4 work in an analogous fashion. Alarm status indicator lights 6, 7 and 8 flash when their respective alarm limits are exceeded. Lights 6–8 flash irrespective of whether the audio alarm is enabled or disabled by alarm inhibit button 5.

Recall that in the absence of parameters exceeding alarm limits, speaker 15 is emitting a pulsed tone whose frequency of repetition equals the patient's pulse rate and whose pitch is proportional to oxygen saturation. When the alarm is enabled by button 5, should any parameter exceed its respective alarm limit, speaker 15 emits a continuous tone of constant pitch until either the alarm is disabled or the parameter comes back within the set boundary. Again, when the alarm is inhibited LED 9 flashes to indicate to the user that audio alarms will not sound.

A more detailed understanding of the oximeter monitor operation discussed so far can be had by reference to the circuitry of FIGS. 15–18. Further understanding may be had by reference to the program listing contained in the microfiche appendix.

Figure 15:
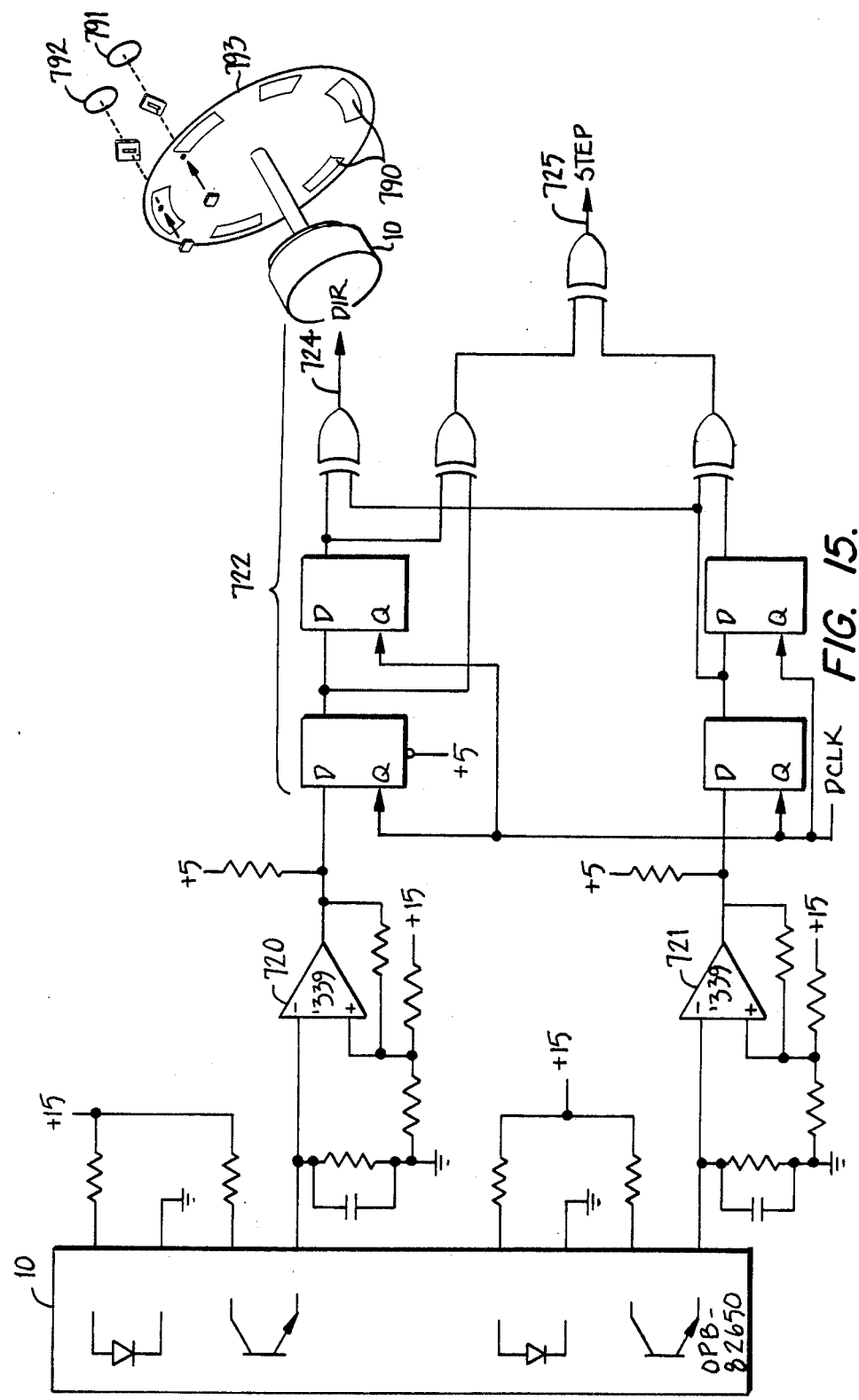
FIG. 15 is a circuit schematic illustrating the operation of the optically coupled adjustment knob.

FIG. 15 is a circuit schematic illustrating operation of the optically coupled control knob 10. Shaft of knob 10 is connected to a shaft encoder 793. Shaft encoder 793 is pierced at regular intervals by windows 790. LED-photosensor pairs are placed in proximity to each other on opposite sides of encoder 793. Pair 792 is shown optically coupled through a window 790 while pair 791 is blocked by encoder 793. The width of each slot is half of the interval between them. Each pair is also equipped with a narrow slit to improve resolutions. The relationship between LED-photosensor pair 791 and 792 is such that they are separated by an angle representing 25% of the slot-to-slot angle, a relationship known as quadrature.

Were encoder 793 to be rotated in a clockwise direction, pair 791 would remain occluded at the point in time when 792 became occluded, whereas if rotated counter clockwise the opposite would be true, that is 791 would be non-occluded when 792 became occluded. A similar unambiguous relationship exists between the two pairs of LED-photosensors for each edge of each window. In such manner, signals may be sent to microprocessor 16 which indicate the direction of rotation and step of knob 10.

Signals from optically coupled pairs, such as pair 791, are presented to comparators 720 and 721. Through control logic 722, both the direction of turn and the step of knob 10 is presented to the microprocessor. Signal on output DIR 724 enables the microprocessor 16 to calculate direction of turn and signal on output STEP 725 enables determination of step. The advantage of this particular arrangement is that the absolute position of the knob 10 becomes immaterial. Only when the microprocessor 16 is receiving signals from a changing knob position does the position of the knob 10 have any import.

Figure 16:
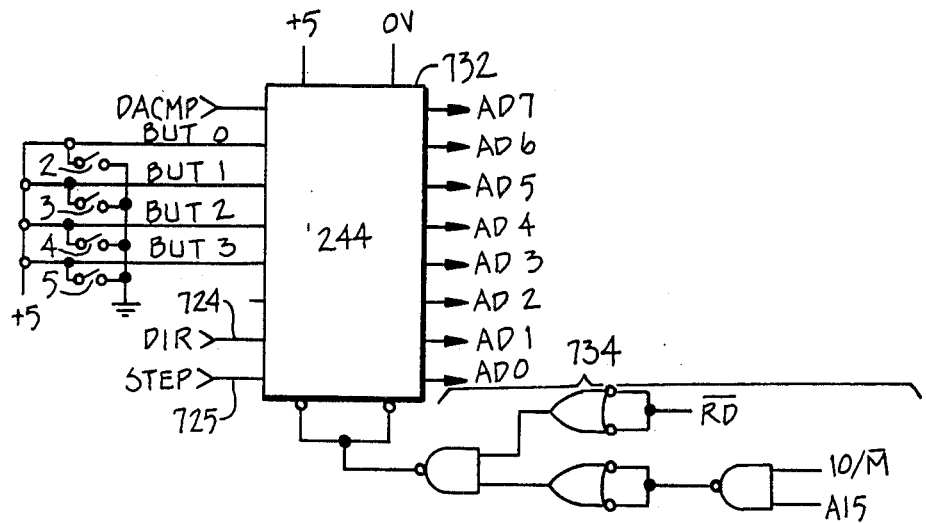
FIG. 16 is a view of the control button circuitry of this invention.

Referring to FIG. 16, direction signal 724 and step signal 725 are passed to input gate 732. Chip 732 is enabled through control logic 734. Inputs from buttons 2–5, in combination with direction signal 724 and step signal 725, output through bus AD0–AD7 to give, in turn, direction and amount of alarm limit correction in RAM memory.

Figure 17:
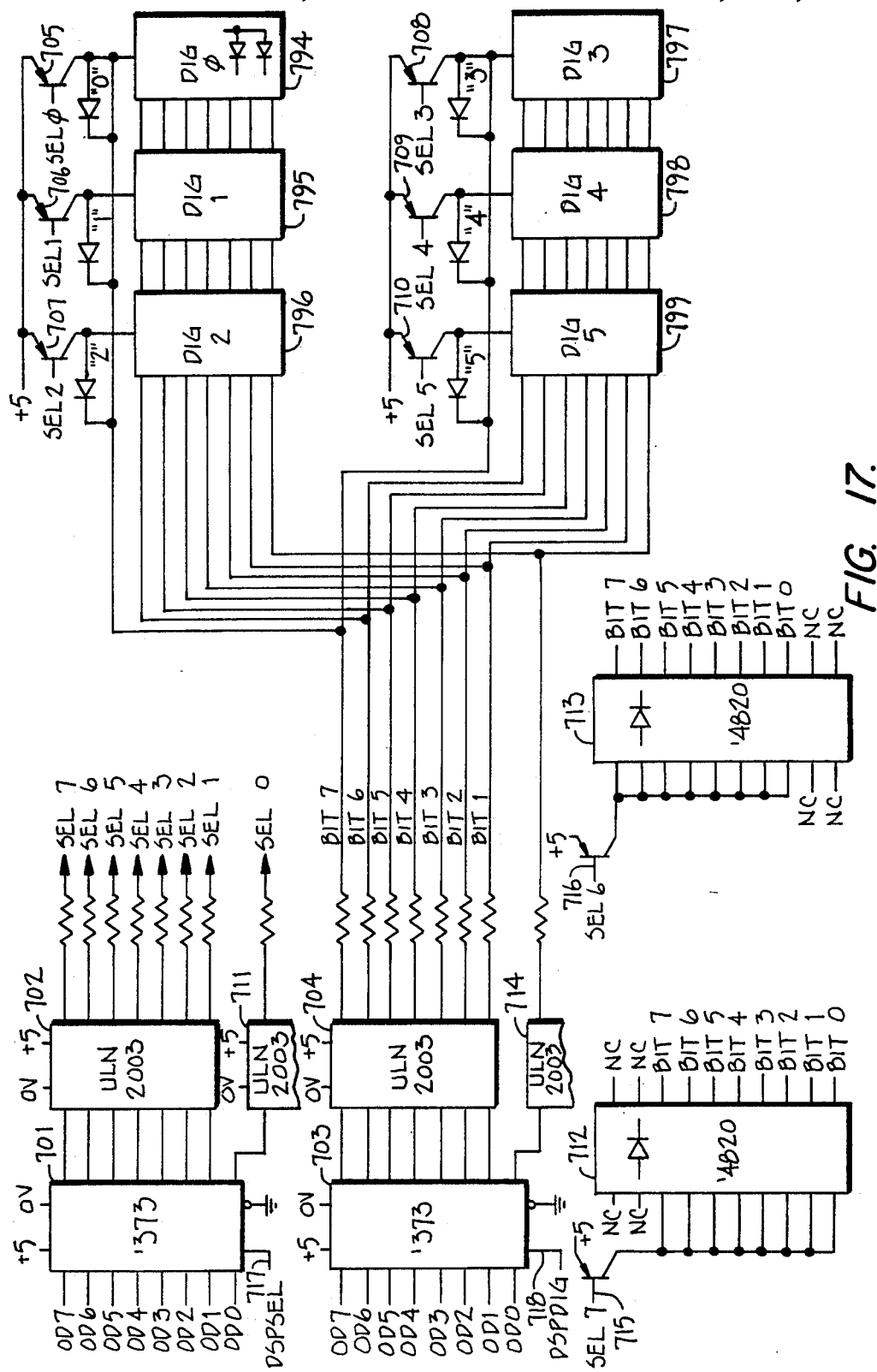
FIG. 17 is a view of L.E.D. circuitry outputs.

Referring to FIG. 17, the LED display circuitry is therein illustrated. Digit selection data presented on data lines OD0–OD7 enters latch 701 enabled by display select DSPSEL 717. The data is outputed to driver 702 and driver 711 to derive numerical digit select signals SEL 0 through SEL 7, 705–710. SEL 0 through SEL 5 enable 7 segment LED decimal numerical displays 794–799.

Data representing the numerical values to be displayed on digits 794–799 enters latch 703, enabled by a display digit DSPDIG 718. The outputs of latch 703 are inputed to drivers 704 and 714. The output of drivers 704 and 714, bit 0 through bit 7, switch on segments of the individually selected standard 7 segment LED display, presenting 1 decimal digit of the current oxygen saturation level or limit, or the current pulse rate level or limit. The other digits are displayed, in turn, in similar fashion.

SEL 7 715 and SEL 6 716 each operate 8 LEDs per chip of LED chips 712, 713. The number of LEDs per chip lit is determined by bit 0 through bit 7. The number of LEDs lit will be proportional to the pulse strength and the rate of flashing of displays 712, 713 is synchronous to heart rate, as discussed above.

Figure 18:
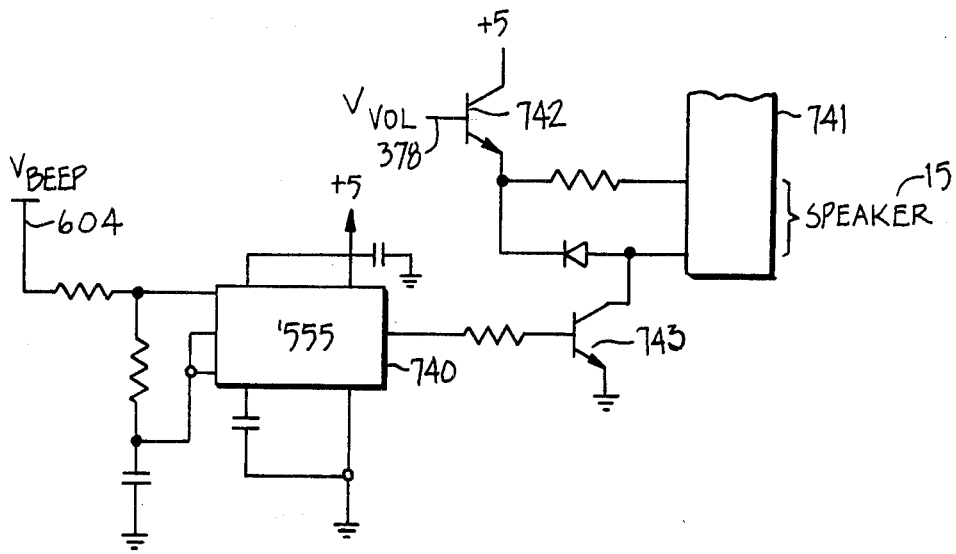
FIG. 18 is a view of the audio output circuitry.

Finally, FIG. 18 illustrates control of the audio output of speaker 15. Voltage levels VVOL 378 and VBEEP 604 (see FIG. 10) correspond to desired volume and desired pitch, respectively. Passing VBEEP 604 to timer 740 and transistor 743 to speaker 15 via connector 741, results in a modulated pitch and tone repetition rate. Passing VVOL 378 to transistor 742 and connector 741 to speaker 15 modulates the volume of the tone.

THEORY OF OPERATION

The method of operations involves taking measurements of light transmission in tissue at two distinct wavelengths (red and infrared) at two arbitrary points in time, these points in time being but a small fraction of the time for a complete pulse. The wave form of a pulse of blood in the human flesh is digitally plotted. By considering the change in the transmission of light due to inflowing arterial blood, a measurement is made.

Regarding this transmission, as blood flows in, light is absorbed. Consequently the resident detector of light, photosensor 38, sees less light. Thus, it is the drop in light received at the photosensor that indicates the pulsatile component.

Assuming that the ambient transmission (approximately 99% of the signal) is represented by the letter I and the change in transmission during the pulse is defined by the letter $\Delta I$ then the equation for representing the change in transmission relative to the unchanging matter in the flesh to be integrated is represented by the equation:

$$\frac{\Delta I}{I} \, \alpha \Delta M \tag{1}$$

where $\Delta M$ is the change in material in the flesh during the pulse.

Interposing a constant to produce an equation yields the form:

$$\frac{\Delta I}{I} = K \Delta M \tag{2}$$

where K is a constant of proportionality in the resultant equation.

Realizing that the change in mass is composed of blood whose optical absorption is larger than the tissue and that this blood includes two forms of hemoglobin: oxy-hemoglobin (hemoglobin with appended oxygen) and reduced hemoglobin (hemoglobin without oxygen), this equation can be expanded for two variants of matter thus:

$$\frac{\Delta I}{I} = K_A \Delta M_A + K_B \Delta M_B \tag{3}$$

where $K_A$ is a constant for oxy-hemoglobin $\Delta M_A$ is the amount of matter due to the influx of oxy-hemoglobin;

$K_B$ is a constant for reduced hemoglobin and $\Delta M_B$ is the change in reduced hemoglobin.

It will be remembered, that we are conducting our examination at two discrete wavelengths. This being the case, the above relation can be expanded to include the applicable constants at each wavelength thus:

$$\left.\frac{\Delta I}{I}\right|_{\lambda 1} = K_{A1}\Delta M_A + K_{B1}\Delta M_B \tag{4a}$$

$$\left.\frac{\Delta I}{I}\right|_{\lambda 2} = K_{A2}\Delta M_A + K_{B2}\Delta M_B \tag{4b}$$

where $K_{A1}$ and $K_{B1}$ are the respective oxy-hemoglobin and reduced hemoglobin constants at a first wavelength $\lambda 1$ (say the red wavelength) and $K_{A2}$ and $K_{B2}$ and are the constants at a second wavelength $\lambda 2$.

It will be appreciated that each of the constants having the form $K_{xy}$ is a constant that relates the relation of the change of absorption to the total light absorption for a particular color and change of matter due to pulsatile flow.

Realizing that we are after the fraction S (saturation) of oxy-hemoglobin to total hemoglobin then we know that:

$$\Delta M_A = S \Delta M \tag{5a}$$

$$\Delta M_B = (1-S)\Delta M \tag{5b}$$

where $$\Delta M = \Delta M_A + \Delta M_B \tag{6}$$

where S equals the saturation and (1−S) equals the fractional presence of the reduced hemoglobin. Placing this into the previous equation yields the results:

$$\left.\frac{\Delta I}{I}\right|_{\lambda 1} = K_{A1}S\Delta M + K_{B1}(1 - S)\Delta M \tag{6a}$$

$$\left.\frac{\Delta I}{I}\right|_{\lambda 2} = K_{A2}S\Delta M + K_{B2}(1 - S)\Delta M \tag{6b}$$

It can be seen from the above equations that once saturation is determined, solution for blood perfusion ($\Delta M$) is trivial.

At this juncture, we surprisingly define a ratio related to the light transmission at two different wavelengths. In defining this ratio, the reader will realize that we avoid manipulation in accordance with logarithmic proportionality. Specifically, we define the ratio between light transmitted and received at the wavelength $\lambda 1$ and at the wavelength $\lambda 2$ as follows:

$$R = \frac{\left.\frac{\Delta I}{I}\right|_{\lambda 1}}{\left.\frac{\Delta I}{I}\right|_{\lambda 2}} \tag{7}$$

Substituting the values of change of light absorption over total light transmission yields:

$$R = \frac{K_{A1} S + K_{B1} - S K_{B1}}{K_{A2} S + K_{B2} - S K_{B2}} \tag{8}$$

Likewise, substituting for S yields:

$$S = \frac{K_{B1} - R K_{B2}}{R(K_{A2} - K_{B2}) - (K_{A1} - K_{B1})} \tag{9}$$

Thus, it can be seen that a relationship exists for both the ratio R and the saturation S.

Those in the medical arts will realize that the numbers sought to be determined electronically by the absorption of light, are also capable of laboratory tests. Specifically, there are a number of laboratory protocols and tests whose accepted results yields saturation. This being the case, a procedure for the calibration of all instruments becomes immediately apparent.

Specifically, by taking laboratory arterial oxygen saturations from individuals at differing saturations $S_1$, $S_2$, $S_3$, and $S_4$, we can measure specific transmission ratios $R_1$, $R_2$, $R_3$, and $R_4$. To reliably obtain these ratios $R_i$, the present instrument itself is used, in particular the portion of the device related to obtaining reliable measurements at hand herein. We thereafter can make an initial guess as to coefficients for both oxy-hemoglobin and reduced hemoglobin.

Taking one of the aforementioned constants $K_{A1}$, this constant can be broken down into two discrete components. First, one component can come from a previously determined value and be denominated $C_{A1}$. Secondly, and for each instrument, this constant will of necessity change. This change will be due to the conditions of observation, individual instrument electronics and the like. This value can be express $\Delta C_{A1}$. Each of the four constants in the above equation can likewise be expanded in the same way.

$$(C_{A2}+\Delta C_{A2})(S_i R_i)+(C_{B2}+\Delta C_{B2})(R_i-S_i R_i)= \\ (C_{A1}+\Delta C_{A1})((S_i)+(C_{B1}+\Delta C_{B1})(1-S_i) \tag{10}$$

where i is an index related to at least four measured saturations and transmission ratios.

Those skilled in math and instrument calculation can now see that the $\Delta C$ quantities in all states and wavelengths can be simultaneously solved provided that four independent saturations are utilized. Therefore, a set of constants is attained, which constants can be utilized for programming individually produced instruments at all values of S.

The aforegoing relations can be alternatively stated. We have found that the relation of R (the ratio of transmission) to S (saturation of the hemoglobin with oxygen) is capable of simple curve fitting. Specifically, for at least human beings a constant and predictable curve of S with respect to R results. By utilizing this relationship in a look-up table, one may quickly compute the saturation of a patient.

Note that in our device, unlike in the prior art, a light source of isobestic wavelength is not used, nor is apparatus for taking logarithms necessary (see equation 7).

The reader will realize that the disclosed pulse oximeter or plethysmograph is targeted for use typically on a human digit. It should be realized that the disclosed pulse oximeter works equally well on any number of cutaneous locations. Idealized and a preferred use of the extremely small and local sensor of this invention is on the scalp of children being born. Avoidance of oxygen poor conditions during birth resulting in cerebral palsy is contemplated. Likewise, any other cutaneous location will suffice, e.g. the nasal septum.

THEORY OF MONITOR CONFIDENCE LIMITS

Figure 19:
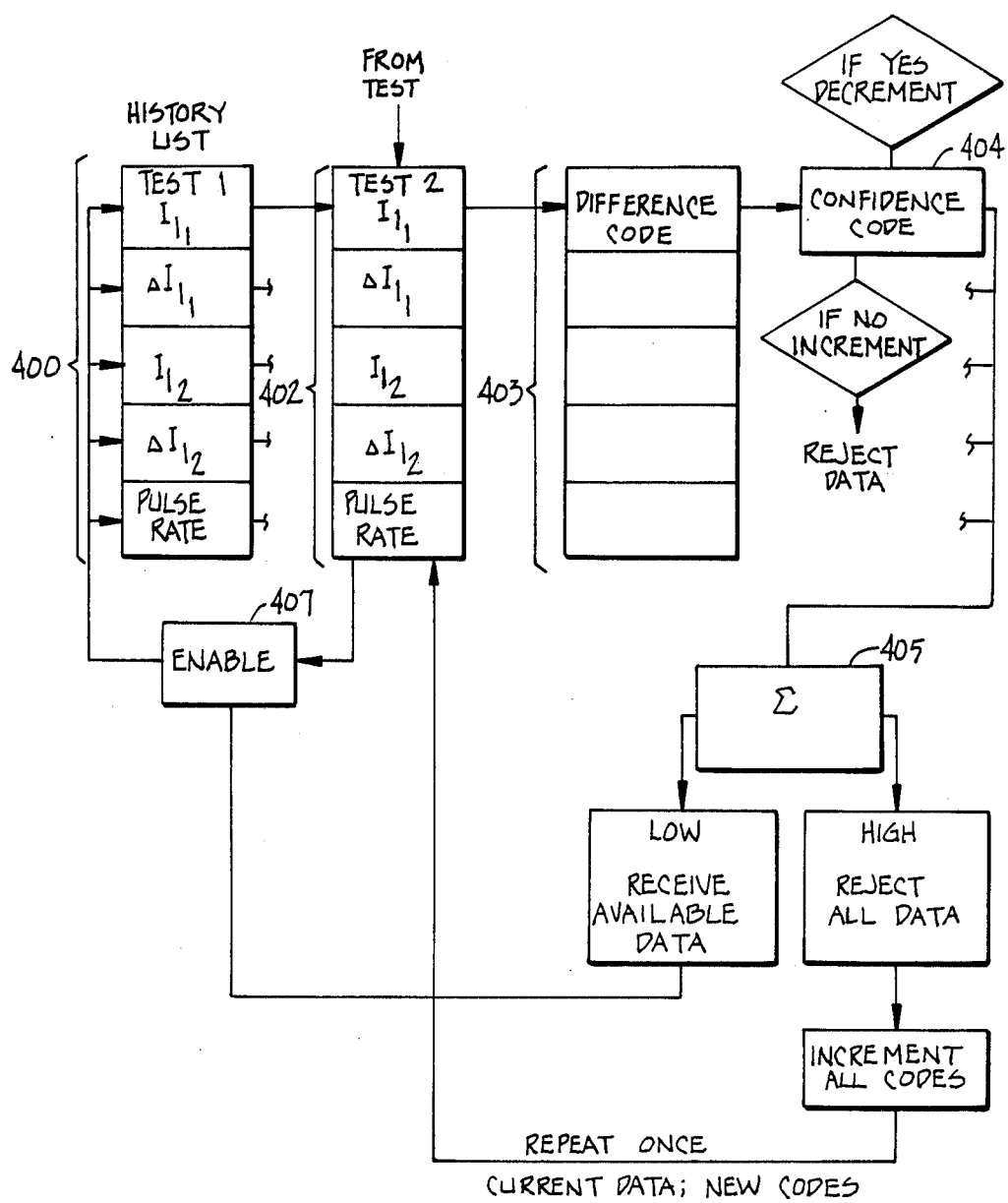
FIG. 19 is a block logic diagram of the numerical process steps which result in the instrument output.

In order to provide an "intelligent" separation of the patient's pulses from noise and motion artifacts, a method of storing expected pulse characteristics and comparison to potential pulse wave forms is employed. This method requires five "vectors" or lists of parameters. These parameters are $\Delta I_{\lambda 1}$, $I_{\lambda 1}$, $\Delta I_{\lambda 2}$, $I_{\lambda 2}$, and the pulse rate and are shown schematically in memory 400 of FIG. 19. It should be noted that these parameters are the same as the transmission parameters described above with scaling appropriate to 16-bit binary arithmetic.

A set of historical values for each parameter is stored in RAM, the history list. Each of these lists is five elements long in the present application, but could be shortened or expanded as required. The history lists are used as references for the current parameters being tested, also stored in RAM. This comparison yields a set of differences, which are similarly stored in coded form as difference codes. Associated with each parameter is also a "confidence" code which is, in essence, a tolerance level for each current parameter, as will be described below.

The first step in the confidence checking is to store the current parameters and then to compare the value of these parameters with the values stored in the history list. Note that the contents of the history list presumably contain the previous good pulse parameters. In the start up condition these pulse parameters are loaded with arbitrary initial values, and associated with a low confidence code admitting wide variations of data. Here, the parameter of total light transmission $I_{\lambda 1}$ is illustrated stored in memory 402.

Once the difference codes have been computed and placed in memory 403, they are compared with the corresponding stored confidence codes in memory 404. These confidence codes, which have the same range as the difference codes, are a description of how close the current parameter must be to the historical value to be considered acceptable. Both the difference codes and the confidence codes are coded in such a way that a code of 0 represents a difference or tolerance of 0–12%, 1 represents 13–25%, 2 represents 26–37%, and so forth, to the code of 8 which represents a 100% mismatch.

The meaning of this code with respect to this difference is that simply the ratio of the current parameter to the historical parameter, and with respect to the confidence codes, represents the tolerance for the parameter.

Once the confidence codes have been computed for each parameter, they are then summed at register 405 to generate a confidence score for the set of parameters. This total score is then compared to a threshold or a maximum acceptable score. It should be noted that a low score represents a close match to the expected value, and activates an enable 407 which allows data reception.

If the total confidence score is below the threshold, then the program assumes that the pulse is indeed a good pulse and takes a branch to update the confidence codes and exits to process the pulse. If the confidence code is above the threshold all data is rejected.

The confidence codes are individually adjusted by comparing the confidence code with the difference code for each parameter. If the difference code is smaller, then the confidence code is decremented by one count, expressing a higher level of confidence for the next text. If the difference code is larger, reflecting a parameter that was not within tolerance, although the total was satisfactory as a set, then that individual confidence code is incremented, representing an eroded confidence level. This process of incrementing or decrementing is repeated twice if the pulse was successful so that the confidence codes quickly converge on good pulses.

In the event that the score was not acceptable, the program retests all of the parameters except for the pulse period, this being the parameter most likely to go out of bounds from motion induced artifact. Assuming that it still fails, the confidence codes are re-adjusted once as described above in order to erode the confidence levels somewhat in preparation for the next trial.

The program then makes one last check with these updated confidence codes before exiting and rejecting the pulse. The reason for this last check is that the confidence codes which will be applied to the next pulse might as well be applied to the current pulse as well, in the event that the pulse is only slightly outside the acceptable window. This technique provides a good response to changing pulse conditions.

The above description outlines in a general way the confidence code processing used in the oximeter to provide an intelligent processor for physiologically based signals. A more detailed description is contained within the comments of the program listing contained in the microfiche appendix.

The reader will appreciate that the disclosed process is an intermediate step in the indication of the measurement.

In addition, the reader will appreciate that for the purposes of determining the calibration of the instrument in human subjects, the technique of determining measurements of $R_i$ with high levels of confidence use the instrument itself to determine the calibration parameters as outlined herein.

In summary, it can be seen that the pulse oximeter monitor of the present invention provides a wide variety of essential information to attending physicians and in a variety of visual and audio forms. While the above provides a full and complete disclosure of the preferred embodiments of the invention, various modifications, alternate constructions, and equivalents may be employed without departing from the true spirit and scope of the invention. For example, high oxygen saturation limits are needed on applications involving newborn infants to prevent bronchopulmonary dysplasia and retrolental fibroplasia. Provision of an additional alarm limit for high oxygen saturation is well within the scope of this invention. Therefore, the above description and illustrations should not be construed as limiting the scope of the invention which is defined by the appended claims.

What is claimed:

1. An oximeter apparatus for use in measuring pulse rate and oxygen saturation of blood by means of absorption of optical radiation through living tissue comprising:

first and second light sources for emitting light at a first and second wavelength, respectively;

a light sensor;

said light sources and light sensor being adapted to be addressed to said tissue to define a light path through said tissue between said light sources and said light sensor;

means for detecting signals corresponding to light received by said light sensor at each of said first and second wavelengths and for deriving from said signals a pulsatile signal corresponding to a pulsatile characteristic of arterial blood flow and generating a signal corresponding to oxygen saturation of the blood; and means for generating an audible intermittent tone signal, said tone signal generating means further comprising means responsive to said pulsatile signal for controlling the occurrence of said audible tone signal, and means responsive to said oxygen saturation signal for varying the tonal frequency of said audible tone signal with oxygen saturation.

2. The apparatus of claim 1 wherein said means for varying the tonal frequency of said audible signal comprises means for decreasing said tonal frequency with decreasing oxygen saturation.

3. The apparatus of claim 1 further comprising:

an array of lights;

circuit means coupled to receive said pulsatile signal from said detecting means for flashing said lights; and circuit means for varying the number of said lights which are flashed in relation to the intensity of said pulsatile signal.

* * * * *

REEXAMINATION CERTIFICATE (1042nd)

United States Patent [19]

New, Jr. et al.

[11] B1 4,653,498

[45] Certificate Issued  Apr. 18, 1989

[54] PULSE OXIMETER MONITOR

[75] Inventors: William New, Jr., Woodside; James E. Corenman, Alameda, both of Calif.

[73] Assignee: Nellcor Incorporated, Haywood, Calif.

Reexamination Request:
No. 90/001,452, Mar. 1, 1988

Reexamination Certificate for:
Patent No.: 4,653,498
Issued: Mar. 31, 1987
Appl. No.: 867,005
Filed: May 20, 1986

Certificate of Correction issued Mar. 31, 1987.

Related U.S. Application Data

[63] Continuation of Ser. No. 417,312, Sep. 13, 1982, abandoned, which is a continuation-in-part of Ser. No. 414,175, Sep. 2, 1982, abandoned.

[51] Int. Cl.⁴ .............................................. A61B 5/02
[52] U.S. Cl. ..................................... 128/633; 128/666; 128/689
[58] Field of Search .............. 128/633, 634, 666, 689, 128/690

[56]  References Cited
U.S. PATENT DOCUMENTS

| | | | |
|---|---|---|---|
| 2,706,927 | 4/1955 | Wood | 88/14 |
| 3,565,058 | 2/1971 | Mansfield | 128/701 |
| 3,638,640 | 2/1972 | Shaw | 128/2 R |
| 3,658,060 | 4/1972 | Eklof | 128/673 |
| 3,704,706 | 12/1972 | Herczfeld et al. | 128/2 R |
| 3,895,316 | 7/1975 | Fein | 128/696 X |
| 3,998,550 | 12/1976 | Konishi et al. | 356/39 |
| 4,013,067 | 3/1977 | Kresse et al. | 128/2.05 R |
| 4,038,976 | 8/1977 | Hardy | 128/690 |
| 4,052,977 | 10/1977 | Kay | 128/661 |
| 4,109,643 | 8/1978 | Bond et al. | 128/666 |
| 4,167,331 | 9/1979 | Nielsen | 128/633 |
| 4,266,554 | 5/1981 | Hamaguri | 128/633 |
| 4,424,814 | 1/1984 | Secunda | 128/663 |

FOREIGN PATENT DOCUMENTS

| | | |
|---|---|---|
| 1589461 | 3/1970 | France . |
| 53-53184 | 5/1978 | Japan . |
| 8201948 | 6/1982 | PCT Int'l Appl. . |
| 2039364 | 8/1980 | United Kingdom . |

Primary Examiner—Lee S. Cohen

[57]  ABSTRACT

A display monitor is disclosed for a pulse oximeter of the type wherein light of two different wavelengths is passed through body tissue, such as a finger, an ear or the scalp, so as to be modulated by the pulsatile component of arterial blood therein and thereby indicate oxygen saturation. A tonal signal is emitted having a pitch proportional to the ratio of oxygen saturation and a sequential repetition proportional to pulse. A visual cue consisting of an array of strobed light emitting diodes is flashed having a total light output proportional to the magnitude of the pulse and a sequential flashing rate proportional to pulse rate. A systematic rejection of extraneous or irregular detected data prevents undue sounding of alarms.

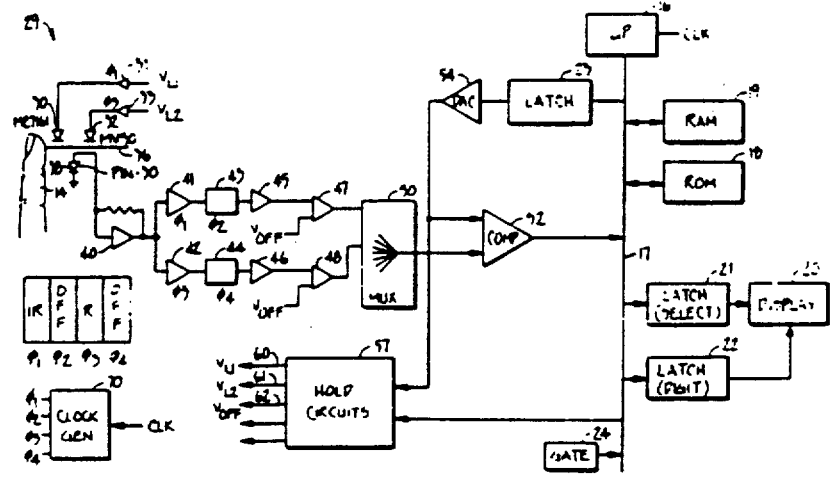

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2 and 3, dependent on an amended claim, are determined to be patentable.

1. An oximeter apparatus for use in measuring pulse rate and oxygen saturation of blood by means of absorption of optical radiation through living tissue comprising:

first and second light sources for emitting light at a first and second wavelength, respectively;

a light sensor;

said light sources and light sensor being adapted to be addressed to said tissue to define a light path through said tissue between said light sources and said light sensor;

means for detecting signals corresponding to light received by said light sensor at each of said first and second wavelengths and for deriving from said signals a pulsatile signal corresponding to a pulsatile characteristic of arterial blood flow and generating a signal corresponding to oxygen saturation of the blood; and means for generating an audible intermittent tone signal, said tone signal generating means further comprising:

means responsive to said pulsatile signal for controlling the occurrence of said audible tone signal, and means responsive to said oxygen saturation signal for *continuously* varying the tonal frequency of said audible tone signal with oxygen saturation.

* * * * *